United States Patent [19]

Kirk

[11] 4,316,323

[45] Feb. 23, 1982

[54] BLADE HOUSING FOR CAST CUTTING TOOL

[76] Inventor: Norbert A. Kirk, 43 E. Ohio St., Room 930, Chicago, Ill. 60611

[21] Appl. No.: 180,363

[22] Filed: Aug. 22, 1980

[51] Int. Cl.³ .............................................. B27B 9/02
[52] U.S. Cl. ...................................... 30/124; 30/377; 144/136 C
[58] Field of Search ............. 30/124, 133, 144, 166 R, 30/377, 276; 83/881; 144/136 C

[56] References Cited

U.S. PATENT DOCUMENTS

| | | | |
|---|---|---|---|
| 1,352,519 | 9/1920 | Laserson | 30/377 |
| 1,641,505 | 9/1927 | Sayre | 30/377 |
| 2,502,656 | 4/1950 | Koett | 30/377 |
| 2,705,513 | 4/1955 | Moeller | 144/136 C |
| 2,823,713 | 2/1958 | Goldsmith | 144/136 C |
| 3,103,069 | 9/1963 | Gary | 30/124 |
| 3,353,266 | 11/1967 | Godsby | 30/377 X |

*Primary Examiner*—Jimmy C. Peters

*Attorney, Agent, or Firm*—Larson and Taylor

[57] ABSTRACT

A blade housing for a cast cutting tool which is used to remove a plaster cast from a patient is provided. The housing is polygonal shaped and includes a number of flat sides through which the circular saw blade of the cast cutting tool projects. The saw blade projects a different distance from each of the flat sides. The housing is attached to the body of the cast cutting tool so that the housing can be rotatably adjusted about the shaft mounting the saw blade. By rotating the housing, a different flat face can be presented to the cutting area. In this manner, the flat face having the desired distance of projection of the saw blade, or the desired depth of the cut, is easily selected by the user. The housing acts to collect the dust generated by the cutting, and to help clean the dust from the blade a felt covering on the flat sides is provided. A dust collecting bag is attached to the housing to provide a receptacle for the dust collected in the housing.

14 Claims, 5 Drawing Figures

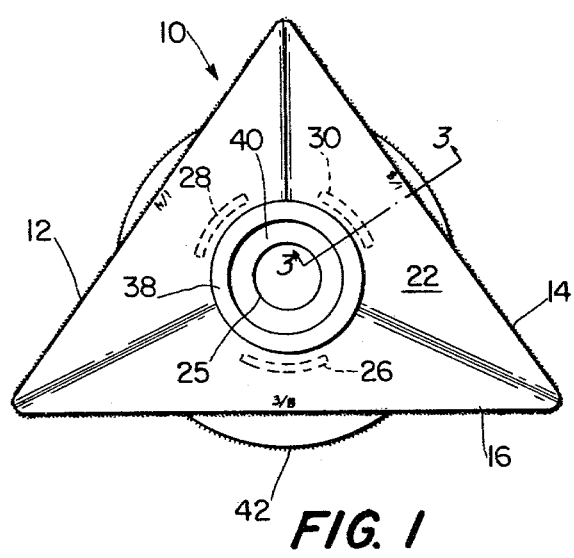
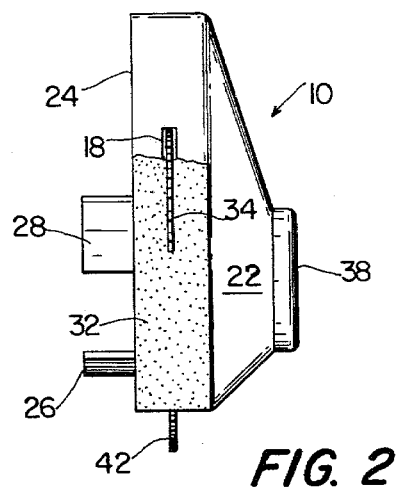
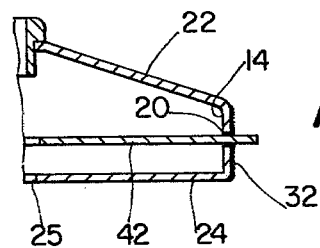
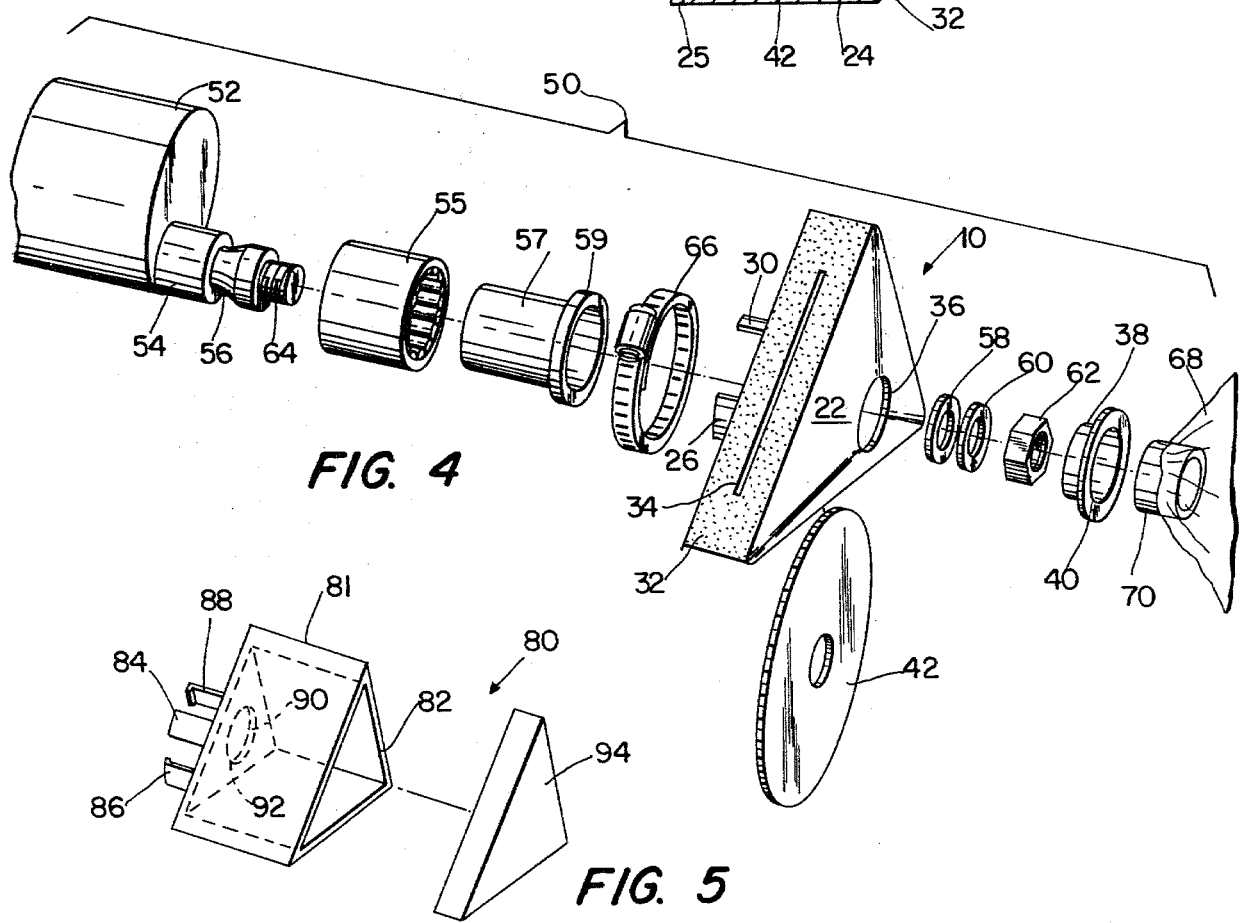

BLADE HOUSING FOR CAST CUTTING TOOL

FIELD OF INVENTION

This invention relates generally to a plaster cast cutting tool and more particularly to a housing for the circular saw blade of the cast cutting tool which determines the depth of the cut.

BACKGROUND OF THE INVENTION

A number of cast cutting tools have been disclosed in the prior art which include means to regulate the depth of a cut of the saw blade. For example, in U.S. Pat. No. 2,374,164 to Castro, a handle assembly containing a saw blade is provided with a substantially rectangular plate or gauge. This plate is eccentrically mounted adjacent the saw blade and bears against the cast as the cast is cut. By rotating the plate, the depth of the cut of the saw blade is determined. Another type of depth regulating device for a cast cutting tool is disclosed in U.S. Pat. No. 2,502,656 to Koett and 1,530,023 to Walton. In these patents, the housing for the saw blade is provided with a projecting foot or the like which is adjustable relative to the housing. The foot is designed to ride along the top of the cast being cut so that by adjustment of the foot relative to the housing, the depth of the cut is determined. Still another type of prior art device has a foot which is adjustable relative to the blade housing which rides underneath of the cast. Such devices are disclosed in U.S. Pat. No. 2,352,432 to Herrington and 2,221,565 to Bailey. In addition to depth cutting gauges, cast cutting tools have also been provided with complicated dust collection means such as disclosed in U.S. Pat. No. 2,399,677 to Hood et al.

There are a number of disadvantages associated with cast cutting tools such as those discussed above. For example, in each of these cast cutting tools with the exception of the device disclosed in the Castro patent, the depth of the cut of the saw blade can only be determined by measurement after the adjustment is made. In addition, the hold-down mechanism for the depth regulating foot is subject to coming loose and allowing the blade to cut deeper into the cast and possibly into the patient. Another disadvantage of the prior art devices is that the saw blade can become clogged with the plaster dust. There is also no provision in the prior art devices for a simple and unobtrusive means to collect the plaster dust generated by the saw blade.

SUMMARY OF THE INVENTION

In accordance with the present invention, an enclosed blade housing for a cast cutting tool is provided which regulates the depth of cut of the saw blade and collects the dust generated by the saw blade. The housing comprises a plurality of rectangular flat sides joined together at their lateral edges to form a polygonal figure. The flat sides are provided with a slot located along a portion of a longitudinal length of each flat side. The circular saw blade is mounted to the cast cutting tool inside of the housing such that the saw blade projects unequal distance from each flat side through the slots. The housing is rotatably attached to the body of the cast cutting tool so that a particular flat side with the desired distance of projection of the saw blade can easily be rotated so as to bear against the surface to be cut.

According to a preferred embodiment, the housing is enclosed so that the dust generated by the saw blade is collected in the housing. The housing is then provided with an aperture to which a dust collecting bag is attached. By tipping the housing appropriately, the dust collected in the housing is deposited in the dust collecting bag. In order to facilitate the cleaning of the saw blade and the depositing of the dust in the housing, each flat side is provided with a felt covering. The felt covering has a slit corresponding to the slot in the flat side, however, the felt covering wipes across the saw blade as it rotates.

Other features and advantages of the present invention are stated in or are apparent from the detailed description of presently preferred embodiments of the invention found hereinbelow.

BRIEF DESCRIPTION OF THE DRAWINGS

FIG. 1 is a front view of the housing for the saw blade of the present invention.

FIG. 2 is a side view of the housing depicted in FIG. 1.

FIG. 3 is a cross-sectional view taken along the line 3—3 in FIG. 1.

FIG. 4 is an exploded perspective view of a plaster cast saw device of the present invention.

FIG. 5 is an exploded perspective view of an alternative embodiment of a plaster collecting receptacle.

DETAILED DESCRIPTION OF THE PREFERRED EMBODIMENT

With reference now to the drawings in which like numerals represent like elements throughout the several views, a presently preferred embodiment of the present invention is depicted in FIGS. 1 and 2 and comprises a housing 10 having three rectangular flat sides 12, 14, and 16. Rectangular flat sides 12, 14, and 16 are joined at their lateral edges to give housing 10 a triangular cross section. Each rectangular flat side 12, 14, and 16 contains a slot along a portion of the longitudinal length thereof, such as slot 18 depicted in FIG. 2 and slot 20 depicted in FIG. 3. A front wall 22 extends slightly forward from side walls 12, 14, and 16 to enclose the front portion of housing 10. Enclosing the opposite end of housing 10 is a rear wall 24. Three arcuate projections 26, 28, and 30 extend outwardly from rear wall 24. Between projections 26, 28 and 30 is an aperture 25 located in the face of rear wall 24. Covering each rectangular flat side 12, 14, and 16 is a layer 32 of felt or similar resilient closure material. At the location of the slot on each rectangular flat side 12, 14, and 16, a slit is provided in felt layer 32 such as slit 34 depicted in FIG. 2. Front wall 22 is provided with an aperture 36 in which a gasket 38 is located. Preferably, gasket 38 is made of resilient rubber so as to be held frictionally in aperture 36 and gasket 38 is provided with a central opening 40.

A circular saw blade 42 is mounted inside of housing 10 so that portions of saw blade 42 extend through the slots in rectangular flat sides 12, 14, and 16. As shown in FIG. 1, saw blade 42 projects from rectangular flat sides 12, 14, and 16 by different distances. For example, saw blade 42 could project from rectangular flat side 12 approximately ⅛ inch, from rectangular flat side 14 approximately ¼ inch, and from rectangular flat side 16 approximately ⅜ inch as indicated by the indicia located on front wall 22.

Depicted in FIG. 4 is a plaster cast saw device 50 including a cast cutting tool 52. A suitable cast cutting tool is model 840-20 manufactured by the Stryker Corporation of Kalamazoo, Mich. While this particular model has a saw blade which oscillates, it should be appreciated that the present invention functions in the same manner whether the saw blade oscillates or rotates. As shown, the body of cast cutting tool 52 has an offset neck portion 54 through which the shaft 56 which mounts saw blade 42 extends. By offsetting shaft 56, a cutting area for saw blade 42 below neck portion 54 remains unobstructed by the remainder of cast cutting tool 52. Saw blade 42 is securely received on shaft 56 by means of a collar 58, shake-proof washer 60, and a threaded nut 62 which is received on a mating threaded end 64 of mounting shaft 56. Housing 10 is mounted on a needle bearing sleeve 55 by means of clamp 66 which fits over projections 26, 28 and 30. Bearing sleeve 55 is rotatably mounted about a steel sleeve 57 having a retaining collar 59. Sleeve 57 is frictionally received on neck portion 54 along approximately three fourths of the length of sleeve 57. Also partially shown in FIG. 4 is a dust collecting bag 68 which is attached to a hollow plug 70.

In order to assemble plaster cast saw device 50, saw blade 42 is first inserted in housing 10 through one of the slots in a rectangular flat side 12, 14 or 16. It should be appreciated that at least one of these slots must therefore be slightly longer than the diameter of saw blade 42. After saw blade 42 is inserted in housing 10, housing 10 is attached to neck portion 54 by means of projections 26, 28 and 30 which are clamped to bearing sleeve 55. Bearing sleeve 55 is then held in place about sleeve 57 by means of collar 59 as sleeve 57 is frictionally received on neck portion 54. In this manner, housing 10 is freely rotatable about neck portion 54. At the same time that housing 10 is positioned on neck portion 54, saw blade 42 is positioned on mounting shaft 56. After housing 10 is secured, collar 58, shake-proof washer 60 and nut 62 are attached to threaded end 64 through aperture 36 in front wall 22. It should be appreciated that saw blade 42 is positioned in housing 10 so as to move through the slots in flat sides 12, 14, and 16. After saw blade 42 is secured, gasket 38 is inserted in aperture 36 where it is frictionally held. Hollow plug 70 is then inserted into gasket 38 so as to mount dust collecting bag 68 in position.

In use, plaster cast saw device 50 functions in the following manner. Before actuation of cast cutting tool 52, the depth to which saw blade 42 is to cut into the cast is determined. Depending on this depth, housing 10 is easily rotated about neck portion 54 until the appropriate rectangular flat side 12, 14, or 16 is presented to the cutting area. The appropriate rectangular side 12, 14, or 16 is determined by the distance which saw blade 42 projects from the side, which is the distance saw blade 42 will cut into the plaster cast. Once the appropriate rectangular flat side 12, 14 or 16 is positioned, this flat side is placed on the cast and moved along the direction of the cut to be made. In this manner, a smooth, even, and precisely regulated depth of cut is obtained in the cast. The rounded corners formed by rectangular side 12, 14, and 16 prevent saw blade 42 from accidently coming into contact with other objects and from catching on small projections in the cast which may be encountered. As housing 10 moves along the plaster cast, felt layer 32 acts as a resilient pad or cushion to make the movement of housing 10 easier.

During the cutting operation, the plaster dust cut from the cast is deposited in housing 10. Depositing of the plaster dust in housing 10 is encouraged by felt layer 32 which wipes along saw blade 42 as saw blade 42 moves through the slit provided in felt layer 32. This wiping action of felt layer 32 also acts to clean saw blade 42. The flying of any dust not collected by housing 10 is also reduced as the dust is trapped between felt layer 32 and the plaster cast. After the dust has accumulated in housing 10, it is transferred to dust collecting bag 68 by tipping cast cutting tool 52 until dust collecting bag 68 is lowermost. Cast cutting tool 52 is then shaken so that the dust will fall onto front wall 22. Front wall 22 extends forward somewhat like a funnel, so that the dust is channelled through gasket 38 and hollow plug 70 into dust collecting bag 68. After quickly transferring the dust from housing 10 into dust collecting bag 68, the cutting of the cast can be resumed immediately. When dust collecting bag 68 is finally full, it is simply removed from gasket 38 and replaced with a new dust collecting bag 68 and hollow plug 70. The filled dust collecting bag 68 is then easily thrown away or emptied for re-use.

As an alternative embodiment, a snap-on case 80 is provided in place of dust collecting bag 68. Case 80 is depicted in FIG. 5 and includes a chamber 81 having three resilient arms 84, 86, and 88. Chamber 81 is shaped similar to and complementary to housing 10 so that front wall 22 of housing 10 fits flush against the rear wall of case 80. Resilient arms 84, 86, and 88 catch behind rear wall 24 of housing 10 to hold chamber 81 removably to housing 10. Inside of chamber 81 is a disposable bag 82 which has an inlet 90. Inlet 90 is aligned with a hole 92 in the rear wall of chamber 81 which in turn is aligned with aperture 36 of housing 10. A front wall 94 is resiliently held onto chamber 81 by the sides of front wall 94 which frictionally fit over the flat sides of chamber 81. Plaster dust is collected in bag 82 from housing 10 by tipping of cast cutting tool 52 in the same manner as described above with respect to dust collecting bag 68. When bag 82 is full, front wall 94 is removed so that bag 82 is easily removed and replaced.

Although the housing of the present invention has been described as having three rectangular flat sides, it should be appreciated that a number of other polygonal figures can also be used to provide additional depths of cut. For convenience, it is also suggested that the different sides be labelled in some manner such as that shown so that the user may easily determine what depth of cut is obtained with each rectangular side. In order for the user to determine when housing 10 is filled with dust, it is recommended that housing 10 be built of a clear or translucent unbreakable plastics material.

As an alternative embodiment, if dust collecting bag 68 and snap-on case 80 are to be omitted, an outlet for the dust collected in housing 10 can be provided at the corner where two rectangular flat sides meet. This outlet can take the form of a hole or a small door covering a larger hole.

In the preferred embodiment, housing 10 has been concentrically mounted about shaft 56. While this is probably the easiest means to mount housing 10, it should be apparent to one skilled in the art that housing 10 could also be mounted eccentrically to shaft 56. It should also be apparent to those skilled in the art that various other means may be employed to rotatably mount housing 10 to cast cutting tool 52.

Thus while the invention has been described in detail with respect to an exemplary embodiment thereof, it will be understood by those of ordinary skill in the art that these and other variations and modifications may be affected in the exemplary embodiment within the scope and spirit of the invention.

I claim:

1. A plaster cast saw device for cutting a cast comprising:
   a cast cutting tool having a body and a movable circular saw blade mounted on a shaft;
   a housing mounted on said body and enclosing said saw blade, said housing having peripheral flat sides such that said housing has a cross-section of polygonal shape and said housing containing a slot in the face of a plurality of said peripheral flat sides through which a portion of said saw blade projects varying distances, whereby the depth of the cut of said saw blade is determined by the side face which is positioned in contact with the cast.

2. A cast saw device as claimed in claim 1 wherein said housing fully encloses said blade except for said slots so as to retain the plaster dust thrown off of said saw blade inside of said housing, and further including an aperture located in said housing located between the side faces, a dust collecting receptacle, and means to attach said receptacle to said aperture so that by appropriate tipping of said device the dust deposited in said housing is collected in said receptacle.

3. A cast saw device as claimed in claims 1 or 2 further including a layer of resilient closure material located on each exterior flat side face of said housing and having a slit corresponding to the slot of each flat side face, said closure material acting to clean the dust from said saw blade as said blade moves through said slit in said resilient closure material.

4. A cast saw device as claimed in claim 3 wherein said resilient closure material is a felt material.

5. A cast saw device as claimed in claim 3 further including means for attaching said housing to said body such that said housing is rotatably adjustable about said shaft.

6. A cast saw device as claimed in claim 5 wherein said means to adjustably attach said housing to said body includes projections which extend from said housing toward said body.

7. A cast saw device as claimed in claim 5 wherein said housing has a triangular cross-sectional shape.

8. A housing for a movable, circular saw blade of a cast cutting tool or the like having a body comprising:
   a plurality of rectangular flat sides joined together at the shorter lateral edges of adjacent sides to form a polygonal figure;
   a slot located in the face of each of said flat sides and extending along a portion of the longitudinal length of each said flat side;
   a front wall attached to said flat sides;
   a rear wall attached to the opposite side of said flat sides from said front wall; and
   means for attaching said rear wall to the body of a cutting tool such that said housing surrounds a circular saw blade and such a saw blade projects unequal distances from said flat sides through said slots and whereby the depth of cut of the saw blade is determined by the flat side face which is positioned in contact with a cast to be cut.

9. A housing as claimed in claim 8 further including an aperture located in said front wall, a dust collecting receptacle having an opening, and means to attach said receptacle to said front wall such that the opening of said receptacle is aligned with said aperture whereby the dust deposited in the housing is collected in said receptacle by tipping the housing appropriately.

10. A housing as claimed in claim 8 or 9 further including a layer of felt located on the exterior of each said flat side, each layer of felt having a slit over said slot of each said flat side whereby said felt acts to clean the dust from the moving saw blade.

11. A housing as claimed in claim 9 wherein there are three of said flat sides which are joined together to form a triangular figure.

12. A housing as claimed in claim 8 wherein said flat sides, said front wall, and said rear wall are all made of a plastic material.

13. A housing as claimed in claim 9 wherein said front wall projects away from said rear wall to form a funnel directed toward said aperture.

14. A housing as claimed in claim 8 further including indicia located adjacent said flat sides to indicate the depth of cut of said saw blade at each flat side.

* * * * *